United States Patent
Takahashi et al.

(10) Patent No.: US 9,526,227 B2
(45) Date of Patent: Dec. 27, 2016

(54) ANIMAL EXCRETION DISPOSAL SHEET

(71) Applicant: UNICHARM CORPORATION, Ehime (JP)

(72) Inventors: Yumei Takahashi, Kagawa (JP); Yasuhiro Sasano, Kagawa (JP); Takayuki Matsuo, Kagawa (JP)

(73) Assignee: Unicharm Corporation, Ehime (JP)

(*) Notice: Subject to any disclaimer, the term of this patent is extended or adjusted under 35 U.S.C. 154(b) by 0 days.

(21) Appl. No.: 14/403,923

(22) PCT Filed: May 29, 2013

(86) PCT No.: PCT/JP2013/064956
§ 371 (c)(1),
(2) Date: Nov. 25, 2014

(87) PCT Pub. No.: WO2013/180190
PCT Pub. Date: Dec. 5, 2013

(65) Prior Publication Data
US 2015/0164041 A1    Jun. 18, 2015

(30) Foreign Application Priority Data

May 31, 2012    (JP) ................... 2012-125379

(51) Int. Cl.
*A01K 1/015* (2006.01)
*A01K 1/01* (2006.01)
(Continued)

(52) U.S. Cl.
CPC .............. *A01K 1/0157* (2013.01); *A01K 1/01* (2013.01); *A01K 1/0107* (2013.01);
(Continued)

(58) Field of Classification Search
CPC ........ A01K 1/0157; A01K 1/01; A01K 1/015; A01K 1/0107; A01K 1/0125; A01K 1/0152; A61L 9/12; E01H 1/1206; A61F 13/4752; A61F 13/49413; Y10T 428/24331; Y10T 428/24231
(Continued)

(56) References Cited

U.S. PATENT DOCUMENTS 3,963,029 A * 6/1976 Brooks ............. A61F 13/49426
604/289
5,342,333 A * 8/1994 Tanzer ................. A61F 13/531
604/358
(Continued)

FOREIGN PATENT DOCUMENTS

CN       1968662 A     5/2007
JP    2005-058167 A    3/2005
(Continued)

OTHER PUBLICATIONS

Chinese Office Action from corresponding Chinese application No. 201380028213.9 dated Nov. 3, 2015 (11 pgs).
(Continued)

*Primary Examiner* — Korie H Chan
(74) *Attorney, Agent, or Firm* — Brinks Gilson & Lione

(57) ABSTRACT

To allow a consumer to easily recall a product image derived from the scent of an animal excretion disposal sheet from the appearance of the product, to thereby improving the product image of the scented animal excretion disposal sheet. The animal excretion disposal sheet including the liquid permeable top sheet, the liquid impermeable back sheet, and the absorbent body disposed between the top sheet and the back surface sheet is configured to be an animal excretion disposal sheet in which the fragrance ingredient is applied to the top sheet or the absorbent body; the evocative information composed of at least one of color, graphic, and character that can evoke the scent of the fragrance ingredient is displayed on the top sheet or the absorbent body; and the
(Continued)

evocative information can be visually recognized from the back sheet side.

13 Claims, 7 Drawing Sheets

(51) Int. Cl.
*E01H 1/12* (2006.01)
*A61L 9/12* (2006.01)

(52) U.S. Cl.
CPC .......... *A01K 1/0125* (2013.01); *A01K 1/0152* (2013.01); *A61L 9/12* (2013.01); *E01H 1/1206* (2013.01)

(58) Field of Classification Search
USPC .......................................................... 119/161
See application file for complete search history.

(56) References Cited

U.S. PATENT DOCUMENTS

| | | | | |
|---|---|---|---|---|
| H001732 H | * | 6/1998 | Johnson | A61F 13/8405 428/131 |
| 6,277,105 B1 | * | 8/2001 | Rynish | A61F 13/5514 604/385.02 |
| 6,761,955 B2 | * | 7/2004 | Mizutani | A61F 13/4752 428/126 |
| 7,891,320 B2 | * | 2/2011 | Otsuji | A01K 1/0107 119/169 |
| 2001/0053899 A1 | * | 12/2001 | Mizutani | A61F 13/511 604/374 |
| 2003/0171726 A1 | * | 9/2003 | Onishi | A61F 13/8405 604/359 |
| 2006/0200105 A1 | | 9/2006 | Takahashi et al. | |
| 2006/0260556 A1 | | 11/2006 | Renforth | |

FOREIGN PATENT DOCUMENTS

| | | |
|---|---|---|
| JP | 3797983 | 4/2006 |
| JP | 2006-238745 A | 9/2006 |
| JP | 2008-206434 | 9/2008 |
| JP | 2012-029625 | 2/2012 |
| JP | 2012-29612 A | 5/2012 |

OTHER PUBLICATIONS

International Search Report from corresponding PCT application No. PCT/JP2013/064956 dated Sep. 3, 2013 (2 pgs).

European extended Search Report from corresponding European application No. 13797281.6 dated May 20, 2016.

* cited by examiner

ANIMAL EXCRETION DISPOSAL SHEET

RELATED APPLICATION

This application is a 35 U.S.C. §371 national phase filing of International Patent Application No. PCT/JP2013/064956 filed May 29, 2013, to which priority is claimed under 35 U.S.C. §120 and through which priority is claimed under 35 U.S.C. §119 to Japanese Patent Application No. 2012-125379, filed May 31, 2012, the complete disclosure of which is hereby expressly incorporated by reference.

TECHNICAL FIELD

The present invention relates to an animal excretion disposal sheet for disposing of excretion of a pet such as a dog or a cat. More specifically, the present invention relates to a scented animal excretion disposal sheet applied with a fragrance ingredient including: a liquid permeable top sheet; a liquid impermeable back sheet; and an absorbent body that is disposed therebetween.

BACKGROUND ART

An animal excretion disposal sheet for disposing of excretion of a pet such as a dog or a cat includes, as basic constituents: a liquid permeable top sheet; a liquid impermeable back sheet; and an absorbent body that is disposed between these sheets. In a case of keeping a pet indoors, the pet needs to be trained to excrete in a pet litter box provided with this type of animal excretion disposal sheet.

Pets such as dogs and cats have the habit of excreting at a place that has an odor. As an animal excretion disposal sheet that makes use of such a habit for litter training, Patent Document 1 proposes a fragrant animal excretion disposal sheet in which a fragrance ingredient is applied uniformly to an entire top sheet (refer to Patent Document 1).

Furthermore, since many pets are kept indoors in recent years, such animal excretion disposal sheets used indoors are required to have an aromatic characteristic which is acceptable for users.

Patent Document 1: Japanese Unexamined Patent Application Publication No. 2008-206434

DISCLOSURE OF THE INVENTION

Problems to be Solved by the Invention

In a conventional scented animal excretion disposal sheet, no particular consideration has been made for allowing consumers to recall the actually applied fragrance based on the appearance of the product. As a result, the actual fragrance is not correctly recalled from the appearance of the product, which hinders improvement of the image of the scented animal excretion disposal sheet.

Given this, the present invention is aimed at allowing a consumer to easily recall a product image derived from the scent of an animal excretion disposal sheet from the appearance of the product, to thereby improve the product image of the scented animal excretion disposal sheet.

Means for Solving the Problems

The present invention is related to an animal excretion disposal sheet including: a liquid permeable top sheet; a liquid impermeable back sheet; and an absorbent body that is disposed between the top sheet and the back sheet; in which a fragrance ingredient is applied to the top sheet or the absorbent body; evocative information composed of at least one of color, graphic, and character that can evoke the scent of the fragrance ingredient is displayed on the top sheet of the absorbent body; and the evocative information can be visually recognized from the back sheet side.

It is preferable that the evocative information can be visually recognized also from the back sheet side.

In addition, it is preferable that the evocative information is an evocative color that can evoke the scent of the fragrance ingredient.

In addition, it is preferable that a combination of the scent of the fragrance ingredient and the evocative color is any one of the following (a) to (f):

(a) the scent of the fragrance ingredient is a soapy scent and the evocative color is a whitish or bluish color;

(b) the scent of the fragrance ingredient is a green tea-like scent and the evocative color is a greenish color;

(c) the scent of the fragrance ingredient is a floral scent and the evocative color is a pinkish or yellowish color;

(d) the scent of the fragrance ingredient is a citrus scent and the evocative color is a yellowish or greenish color;

(e) the scent of the fragrance ingredient is a fruity scent and the evocative color is a pinkish yellowish color; and (f) the scent of the fragrance ingredient is a marine scent and the evocative color is a bluish color.

In addition, it is preferable that the absorbent body is provided with an absorbent core and a top face side core wrapping sheet which is disposed on the top sheet side of the absorbent core, and the evocative information is displayed on the top face side core wrapping sheet.

In addition, it is preferable that a basis weight of the top sheet is at least 23 g/m$^2$ and the sum of the basis weight of the top sheet and a basis weight of the absorbent body is in a range of 59 g/m$^2$ to 232 g/m$^2$.

In addition, it is preferable that the basis weight of the absorbent body is configured to be in a range of 36 g/m$^2$ to 202 g/m$^2$.

In addition, it is preferable that the total light transmittance of the back sheet is in a range of 20% to 90%.

In addition, it is preferable that the total light transmittance is in a range of 40% to 70%.

In addition, the present invention is a package body of an animal excretion disposal sheet including the animal excretion disposal sheet according to any one of the described above and a bag that houses the animal excretion disposal sheet, in which the animal excretion disposal sheet is housed in the bag in a state of being folded such that the back sheet composes an outer face.

In addition, it is preferable that the animal excretion disposal sheet is configured to be folded so as to have an area in which top sheet portions oppose each other and an area in which the top sheet opposes the back sheet, and the fragrance ingredient is applied to the area in which the top sheet portions oppose each other.

In addition, it is preferable that the evocative information is displayed also on the surface of the bag.

Effects of the Invention

According to the animal excretion disposal sheet of the present invention, evocative information that can evoke the scent of the fragrance ingredient applied to the animal excretion disposal sheet can be visually recognized from the back sheet side, to thereby improve the product image of the scented animal excretion disposal sheet.

Figure 1:
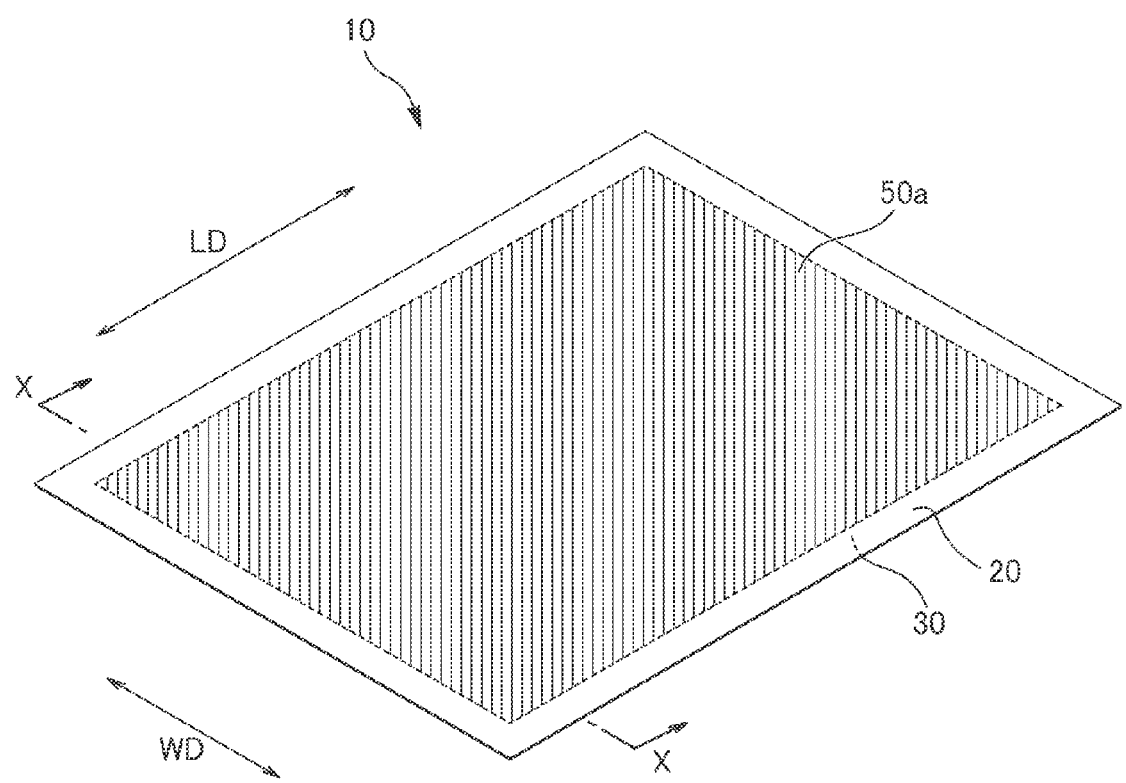
FIG. 1 is a perspective view of the animal excretion disposal sheet of the present invention viewed from a top sheet side.

EXPLANATION OF REFERENCE NUMERALS 10, 11 Animal excretion disposal sheet
20 Top sheet
30 Back sheet
40 Absorbent Body
41 Absorbent core
411 Hydrophilic fiber
412 Water absorbent resin
42 Core wrapping sheet
421 Top face side core wrapping sheet
422 Back face side core wrapping sheet
50, 51, 52 Evocative information
60 Bag
70 Package body

PREFERRED MODE FOR CARRYING OUT THE INVENTION

A preferable embodiment of the animal excretion disposal sheet is described with reference to FIGS. 1 to 6 as required.

Figure 2:
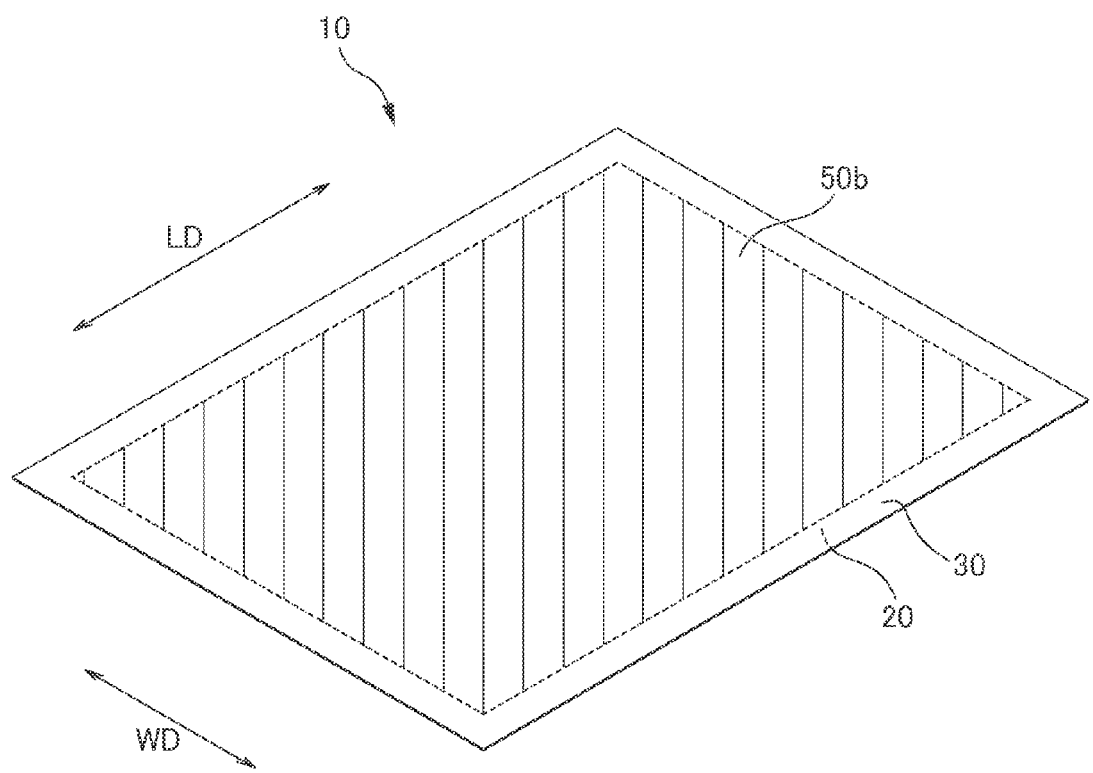
FIG. 2 is a perspective view of the animal excretion disposal sheet of the present invention viewed from a back sheet side.
Figure 3:
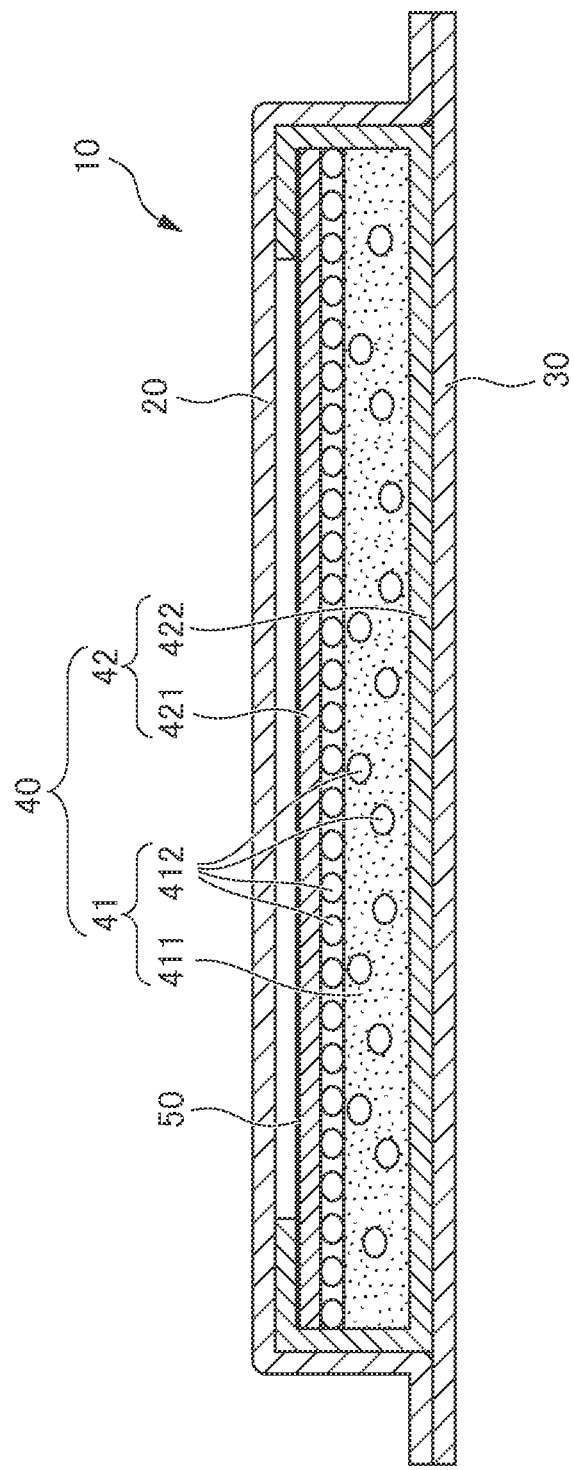
FIG. 3 is a cross-sectional view taken along the line X-X of FIG. 1.

FIG. 1 is a perspective view of an animal excretion disposal sheet 10 according to an embodiment viewed from a side of a top sheet 20 which is a face on which a pet or the like excretes stool and urine during use thereof. FIG. 2 is a perspective view of the animal excretion disposal sheet of the present invention viewed from a side of a back sheet 30; FIG. 3 is a cross-sectional view taken along the line X-X of FIG. 1.

The animal excretion disposal sheet 10 of the present embodiment is formed to be planar as a whole. As shown in FIGS. 1 to 3, the animal excretion disposal sheet 10 includes a liquid permeable top sheet 20, a liquid impermeable back sheet 30, and an absorbent body 40 disposed between the top sheet 20 and the back surface sheet 30 that absorbs and retains liquid such as excreted matter. In addition, in an outer periphery of the animal excretion disposal sheet 10, the top sheet 20 and the back sheet 30 are joined by a hotmelt adhesive.

Furthermore, a fragrance ingredient is applied to at least a part of a region of the top sheet 20 or the absorbent body 40 of the animal excretion disposal sheet 10.

The animal excretion disposal sheet 10 is configured such that evocative information 50 which can evoke the scent of the fragrance ingredient is displayed on the top sheet 20 or the absorbent body 40. Regarding a display position of the evocative information 50, a mode of being displayed on a top face side core wrapping sheet 421 which is disposed in the absorbent body 40 on the top sheet 20 side, as illustrated in FIG. 3, can be exemplified as a preferable example. Here, the evocative information indicates visual information that allows a consumer or the like of the animal excretion disposal sheet 10 to recall an image derived from the scent of the animal excretion disposal sheet 10 from the appearance of the animal excretion disposal sheet 10, upon visually recognizing the information.

As illustrated in FIG. 2, the evocative information 50 (50b) is displayed so as to be visually recognizable from a side of the back sheet 30 of the animal excretion disposal sheet 10. In addition, it is preferable that the evocative information 50 (50a) is displayed to be visually recognizable also from the top sheet 20 side. Since the evocative information 50b is visually recognizable from the back sheet 30 side, the evocative information 50, which is displayed on the animal excretion disposal sheet 10, can be visually recognized by a consumer or the like, even in a state of having been folded with the back sheet 30 directed to an outer face side, for example before start of use. As a result, the product image derived from the scent of the fragrance ingredient being applied can be evoked.

The size of the animal excretion disposal sheet 10 can be selected appropriately according to the size of a target animal and a cage, and is not particularly limited. However, the length in a longitudinal direction (LD) is preferably at least 30 cm and no greater than 120 cm and the length in a width direction (WD) is preferably at least 20 cm and no greater than 100 cm. The area in a plan view is preferably at least 600 cm$^2$ and no greater than 12000 cm$^2$.

The top sheet 20 is disposed to cover the absorbent body 40 and allows liquid such as excretion to pass through to the absorbent body 40. As a material for the top sheet 20, various liquid permeable sheet materials such as a liquid permeable nonwoven fabric are used. More specifically, a thermal bond nonwoven fabric made of hydrophilic polypropylene fiber, a point bond nonwoven fabric, a through-air nonwoven fabric, a spun-lace nonwoven fabric, a spun-bonded nonwoven fabric and the like can be used. By using these materials as the top sheet 20, the excretion and the like can be quickly let through to the absorbent body 40.

The thickness of the top sheet 20 is preferably at least 0.1 mm and no greater than 2.4 mm. The thickness of the top sheet 20 being less than 0.1 mm impairs the property of masking urine and the like absorbed by the absorbent body 40 and provides an inferior appearance during use, and is therefore not preferable. On the other hand, the thickness of the top sheet 20 being greater than 2.4 mm makes visual recognizability of the evocative color 50a insufficient and lowers liquid permeability, and is therefore not preferable.

A basis weight of the top sheet 20 is preferably at least 8 g/m$^2$ and the sum of the basis weight of the top sheet 20 and a basis weight of the absorbent body 40 is preferably in a range of 44 g/m$^2$ to 232 g/m$^2$, and more preferably in a range of 59 g/m$^2$ to 232 g/m$^2$. In addition, the basis weight of the top sheet 20 is more preferably at least 23 g/m$^2$. By making the basis weight of the top sheet 20 at least 8 g/m$^2$, sufficient water absorbent performance can be provided to the animal excretion disposal sheet 10 even if the basis weight of the absorbent body 40 is limited to the predetermined range described below. In addition, by making the basis weight at least 23 g/m², more preferable water absorption performance can be provided while the property of masking excretion absorbed into the absorbent body 40 can be made more preferable. Furthermore, by making the sum of the basis weight of the top sheet 20 and the basis weight of the absorbent body 40 preferably in a range of 44 g/m² to 232 g/m², and more preferably in a range of 59 g/m² to 232 g/m², sufficient water absorbent performance can be provided to the animal excretion disposal sheet 10 while allowing the evocative information 50b to be visually recognized from the back sheet 30 side. It should be noted that the sum of the basis weight of the top sheet 20 and the basis weight of the absorbent body 40 indicates a value obtained by summing the basis weight of the top sheet 20 and values of respective basis weights of material members such as nonwoven fabric, tissue, an absorbent core and the like, which constitute the absorbent body 40, individually measured.

In a case in which an evocative color is displayed as the evocative information 50 on the top sheet 20, a color of the top sheet 20 is the evocative color. In a case in which the evocative information 50 is displayed on the absorbent body 40, the color of the top sheet 20 is preferably white. Whiteness is preferably at least 48%. Even in a case in which the evocative information 50 is displayed on the absorbent body 40, by configuring the top sheet 20 to be white with whiteness within the above described range, the evocative information 50 can be sufficiently visually recognized while maintaining the property of masking urine and the like absorbed into the absorbent body 40. It should be noted that, in the present specification, the whiteness indicates the ISO whiteness (JIS P8148) by diffused illumination.

The back sheet 30 is disposed on aside opposite to the top sheet 20 across the absorbent layer 40, and constitutes a leak-proof layer in the animal excretion disposal sheet 10. As a material for the back sheet 30, various film materials which are substantially liquid impermeable are used. More specifically, a polyethylene air impermeable film and conventionally known resin films such as polypropylene, polyethylene terephthalate and the like can be used as the back sheet.

It is preferable that the above described resin film used as the back sheet 30 is a light transmissive resin film. In the present specification, "light transmissive" indicates that, in a case in which the resin film or the like is used as the back sheet 30 of the animal excretion disposal sheet 10, the resin film or the like is light transmissive to such a degree that the evocative color 50b can be visually recognized from the back sheet 30 side, under brightness of a normal indoor living environment (in the order of 1000 lux). More specifically, as the "light transmissive" resin film, transparent, translucent, and white resin films and the like can be cited as examples. From the viewpoint of design and the property of masking excretion, it is preferable that the resin film is white.

In a case in which the resin film is white, from the viewpoint of optimization of balance between the above described design, the property of masking excretion, and the visual recognizability, whiteness is preferably at least 60%. As such a white resin film, for example, a polyethylene air impermeable film containing 4% to 6% of titanium oxide can be used particularly preferably.

Regarding the total light transmittance of the resin film used as the back sheet 30, more specifically, total light transmittance (according to JIS K7105 measurement method A) of the resin film is required to be in a range of 20% to 90%, and preferably in a range of 40% to 70%. The total light transmittance being at least 20% allows visual recognition of the evocative color 50b from the back sheet 30 side, and the total light transmittance being at least 40% allows clearer visual recognition. On the other hand, the total light transmittance exceeding 90% almost eliminates the property of masking excretion in the absorbent body 40 upon disposal of the pet sheet and may give an unpleasant sensation to a consumer, and is therefore not preferable.

The absorbent body 40 is composed of an absorbent core 41 and a core wrapping sheet 42 that covers the absorbent core 41. The thickness of the absorbent body 40 is preferably at least 0.4 mm and no greater than 2.4 mm. The absorbent body 40 with a thickness less than 0.4 mm has an insufficient absorption property. On the other hand, the absorbent body 40 with a thickness greater than 2.4 mm may make the visual recognizability of the evocative color 50b from the back sheet 30 side insufficient, is bulky and requires more space for storage, and is therefore not preferable. In order that the evocative color 50b may be visually recognizable from the back sheet 30 side while maintaining necessary water absorbent performance, a basis weight of the absorbent body 40 is preferably in a range of 36 g/m² to 202 g/m² and more preferably in a range of 86 g/m² to 157 g/m². In addition, it is more preferable that a basis weight of the absorbent core 41 alone is in a range of 59 g/m² to 128 g/m². It should be noted that, as described above, the sum of the basis weight of the top sheet 20 and a basis weight of the absorbent body 40 is preferably in a range of 44 g/m² to 232 g/m², and more preferably in a range of 59 g/m² to 232 g/m².

The absorbent core 41 is configured to include a hydrophilic fiber 411 and/or a water absorbent resin 412. It is preferable that most of the water absorbent resin 412 is spread so as to be dispersed substantially uniformly in a layer formed of the hydrophilic fiber 411. Furthermore, it is more preferable that another portion of the water absorbent resin 412 is spread substantially uniformly at an interface between the layer formed of the hydrophilic fiber 411 and a top face side core wrapping sheet 421. By applying a portion of the water absorbent resin 412 to the interface, dispersion of excreted urine on the top sheet 20 can be suppressed properly and the number of times the animal excretion disposal sheet 10 is reused can be increased.

As the hydrophilic fiber 411, conventionally known hydrophilic materials are used. More specifically, a cellulosic fiber such as fluff pulp or other pulp, regenerated pulp or wood powder can be used. It is preferable that these hydrophilic materials have a water retention capacity of no greater than 4 times of their own weight. As used herein, "water retention capacity" indicates the remaining amount of absorbed water after immersing 5 g of a material used as the hydrophilic fiber 411 in water for 10 minutes and then performing centrifugal dehydration thereof at 150 G for 90 seconds, and is evaluated by the ratio of the remaining amount of absorbed water to the material's own weight. By setting the water retention capacity of the hydrophilic fiber 411 within the above described range, a preferable absorption performance can be provided to the absorbent body 40.

As the water absorbent resin 412, a polymeric absorbent body is used. More specifically, a resin that is generally highly absorbent such as polyacrylic acid polymer, starch-acrylic acid polymer or the like can be used. Here, absorbing speed of the water absorbent resin 412 is preferably high, more specifically preferably no greater than 20 seconds as measured by the vortex method. By setting the absorbing speed of the water absorbent resin 412 within the above described range, a preferable absorption performance can be provided to the absorbent body 40. It should be noted that the value of the vortex method is obtained by measurement by the following steps.

1) setting a 0.9% sodium chloride solution (first grade reagent) to 25 C±1 degrees C.;
2) putting a rotor and 50 g of the solution of 1) in a 100 ml beaker and agitating at 600 rpm;
3) adding 2 g of water absorbent resin to be measured and measuring the time until liquid surface movement stops due to imbibition, as seconds vortex.

The core wrapping sheet 42 is composed of the top face side core wrapping sheet 421 and a back face side core wrapping sheet 422. The back face side core wrapping sheet 422 has lateral edges that rise up so as to wrap the entire absorbent body 40. In addition, a front end portion of the absorbent body 40 is arranged to overlap an end portion of the top face side core wrapping sheet 421.

It should be noted that the core wrapping sheet 42 can be in any configuration that allows wrapping of the entire absorbent core 41 and is not limited to the above described configuration. For example, the core wrapping sheet can be composed of a single sheet of water absorbent paper. In the present specification, a part of the core wrapping sheet that is disposed on the top sheet 20 side is referred to as the top face side core wrapping sheet, even in a case in which the part cannot be recognized as an independent constituent member.

As the core wrapping sheet 42, a sheet member composed of hydrophilic paper or fiber is used. More specifically, a tissue made of bleached softwood kraft pulp can be used.

As illustrated in FIG. 2, on the animal excretion disposal sheet 10, the evocative information 50b is displayed so as to be visually recognizable from a side of the back sheet 30. In addition, it is preferable that the evocative information 50a is displayed to be visually recognizable also from the top sheet 20 side. A shaded part (the evocative information 50a) on the top sheet 20 in FIG. 1 and a shaded part (the evocative information 50b) on the back sheet 30 in FIG. 2 schematically indicate that the evocative information 50, which is a color that can evoke the scent of the fragrance ingredient, is visually recognizable in respective shaded parts, from respective sides. It should be noted that, in the present specification, in a case in which the evocative information 50 is a specific color that can evoke the scent of the fragrance ingredient, the specific color is also referred to as an evocative color. It should be noted that, in a case in which the evocative information 50 is a graphic, the information is also referred to as an evocative graphic; and in a case in which the evocative information 50 is a character, the information is also referred to as an evocative character. The evocative information can be any one of, or a combination of two or more of, the evocative color, the evocative graphic, and the evocative character. A case in which the evocative information 50 is the evocative color is described hereafter.

A method and an area of coloring of the evocative color 50 on the top sheet 20 or the absorbent body 40 are not particularly limited as long as the evocative color can be visually recognized from both the top sheet 20 side and the back sheet 30 side of the animal excretion disposal sheet 10. However, in order to enhance the effect of improving the product image, the evocative color is preferably applied to the entire surface of the top face side of the top sheet 20 or the top face side core wrapping sheet 421.

The evocative color can be displayed to be visually recognizable also by employing a material that has been colored in the evocative color in advance, as a material constituting the top sheet 20 or the absorbent body 40. For example, the evocative color of the animal excretion disposal sheet 10 can be displayed to be visually recognizable without any additional step in a manufacturing process, by employing colored tissue that has been colored in the evocative color in advance as a material for the top face side core wrapping sheet 421.

An appropriate amount of a fragrance ingredient is applied to at least a part of a region of the top sheet 20 or the absorbent body 40 in the animal excretion disposal sheet 10. A range to which the fragrance ingredient is applied can be any of the above described regions. Applying the fragrance ingredient to a part of a region of the top sheet 20 is preferable due to being able to apply the fragrance by a relatively easy step. Applying the fragrance ingredient to a part of a region of the absorbent body 40 is preferable due to being able to make a scent be perceived sufficiently by a consumer and to suppress dissipation of the fragrance ingredient before use more effectively than in a case of applying the fragrance ingredient to the top sheet 20.

The type of the fragrance ingredient is not particularly limited. In the animal excretion disposal sheet 10, fragrance including well-known fragrance ingredients having been used for scented animal excretion disposal sheets can be used. It should be noted that since the animal excretion disposal sheet 10 is generally used indoors, the fragrances are required to be of a scent type and intensity that are agreeable for indoor users.

Here, representative specific examples of combinations of the fragrance which can be preferably used for the animal excretion disposal sheet and the evocative color which can evoke the scent of the fragrance are presented in the following Table 1. The combination of the fragrance and the evocative color can be any combination that allows the consumer to recall the scent of the fragrance upon visually recognizing the evocative color. The combination is not limited to the combinations presented in Table 1. However, by employing the combinations presented in Table 1 including fragrances which have been practically used as fragrances for animal excretion disposal sheets, the animal excretion disposal sheet 10 can be an animal excretion disposal sheet that allows the consumer to easily and reliably recall the product image derived from the scent from the appearance thereof.

TABLE 1

| Fragrance (Name of Compound) | Scent | Evocative Color |
| --- | --- | --- |
| Musk | Soap-like Scent | White, Blue |
| Cis-3-hexanol | Green tea-like Scent | Green |
| Phenylethyl alcohol | Floral Scent | Pink, Yellow |
| Limonene | Citrus Scent | Yellow, Green |
| Lactone | Fruity Scent (Peach etc.) | Pink, Yellow |
| Melonal, Calone | Marine scent | Blue |

Figure 4:
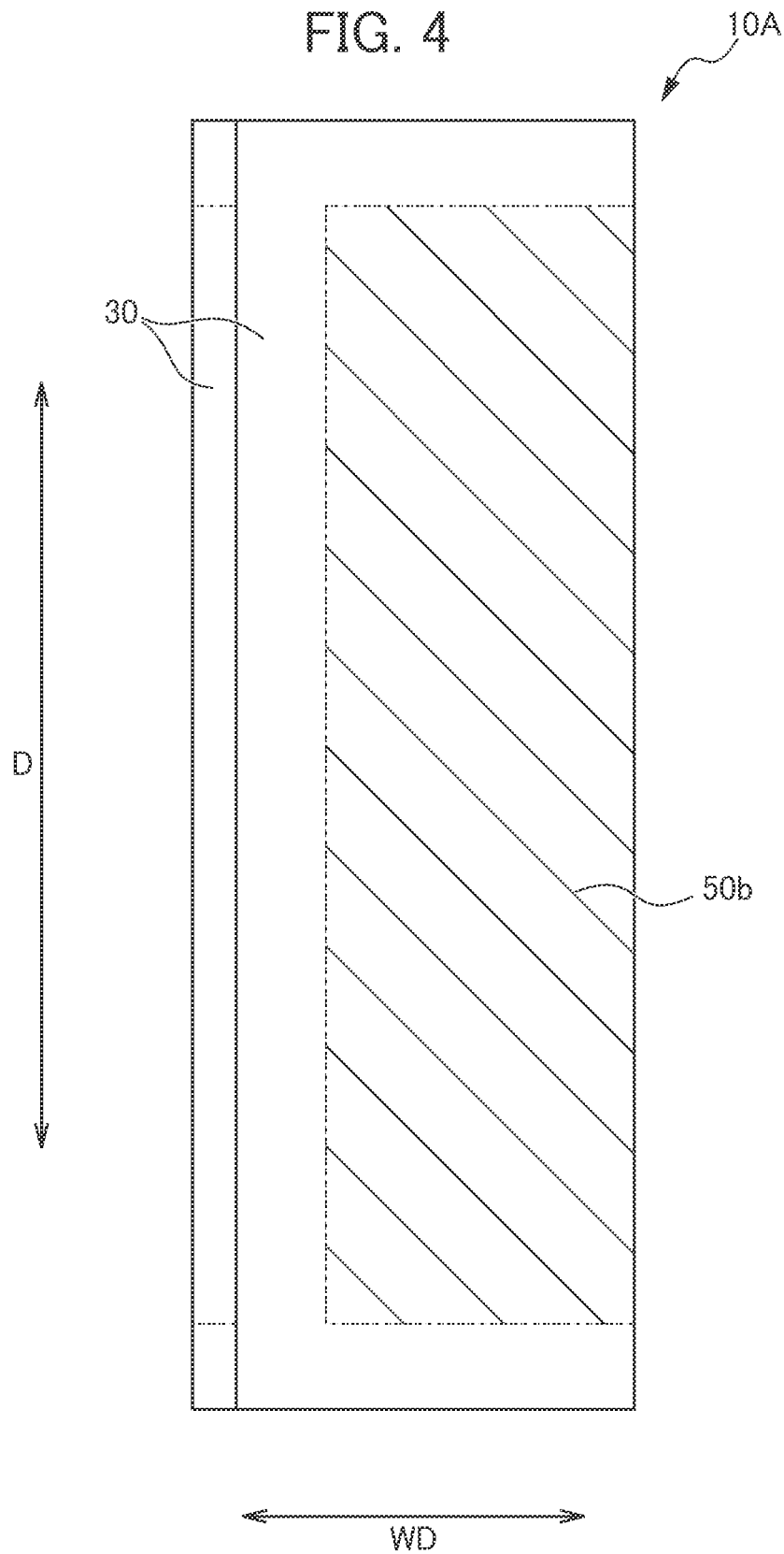
FIG. 4 is a plan view of the animal excretion disposal sheet of the present invention in a state of being folded in a preferable mode.

The animal excretion disposal sheet 10 described above is generally distributed in a state of a package body in which the sheet is folded and packaged in a bag or the like. It is preferable that, in a state of being packaged in the package body, the animal excretion disposal sheet 10 is folded, for example triple folded, so as to have an area in which top sheet 20 portions oppose each other and an area in which the top sheet 20 opposes the back sheet 30. FIG. 4 is a plan view of the animal excretion disposal sheet 10 in a state of being triple folded so that the back sheet 30 constitutes an outer face. Even in the animal excretion disposal sheet 10 having been folded in the above described mode, the evocative information 50 (50b) can be visually recognized from a side of the back sheet 30 and can allow a consumer or the like to easily recall an image derived from the scent.

The case in which the evocative information 50 is the evocative color has been described; however, the evocative information 50 in the animal excretion disposal sheet can also be a graphic or a character.

Figure 5:
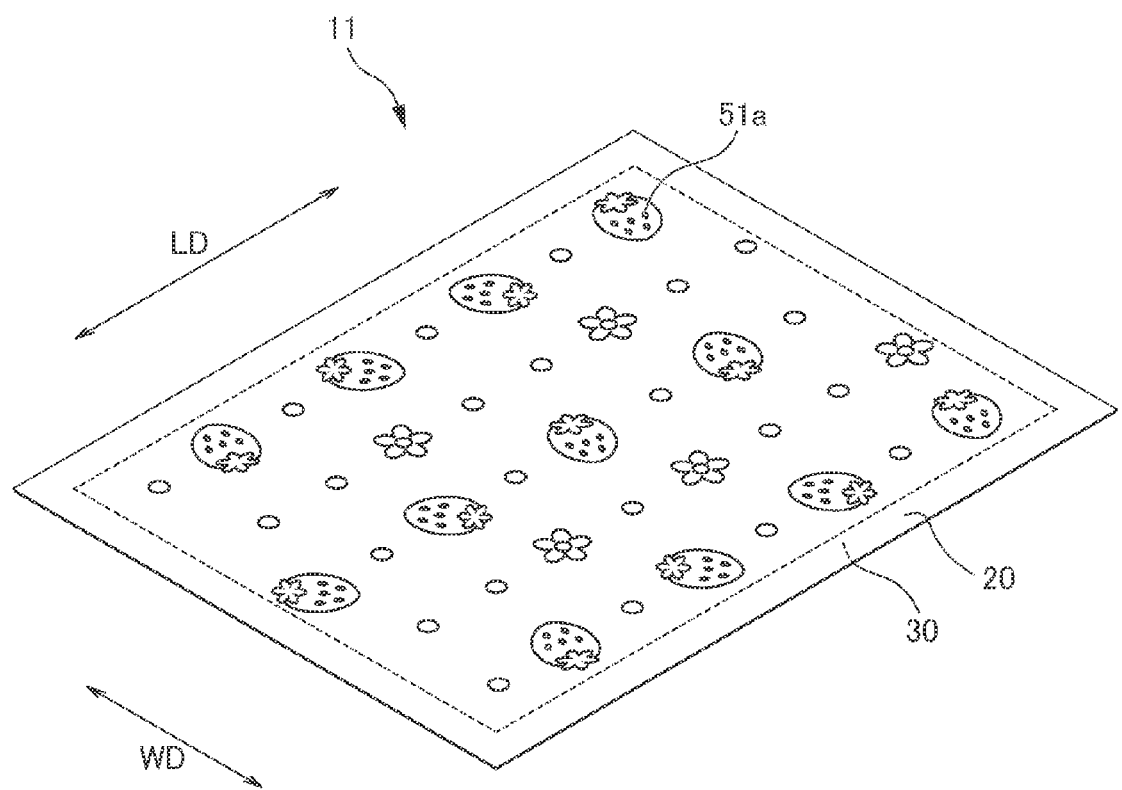
FIG. 5 is a perspective view of the animal excretion disposal sheet of the present invention provided with an evocative pattern as the evocative information, viewed from the top sheet side.
Figure 6:
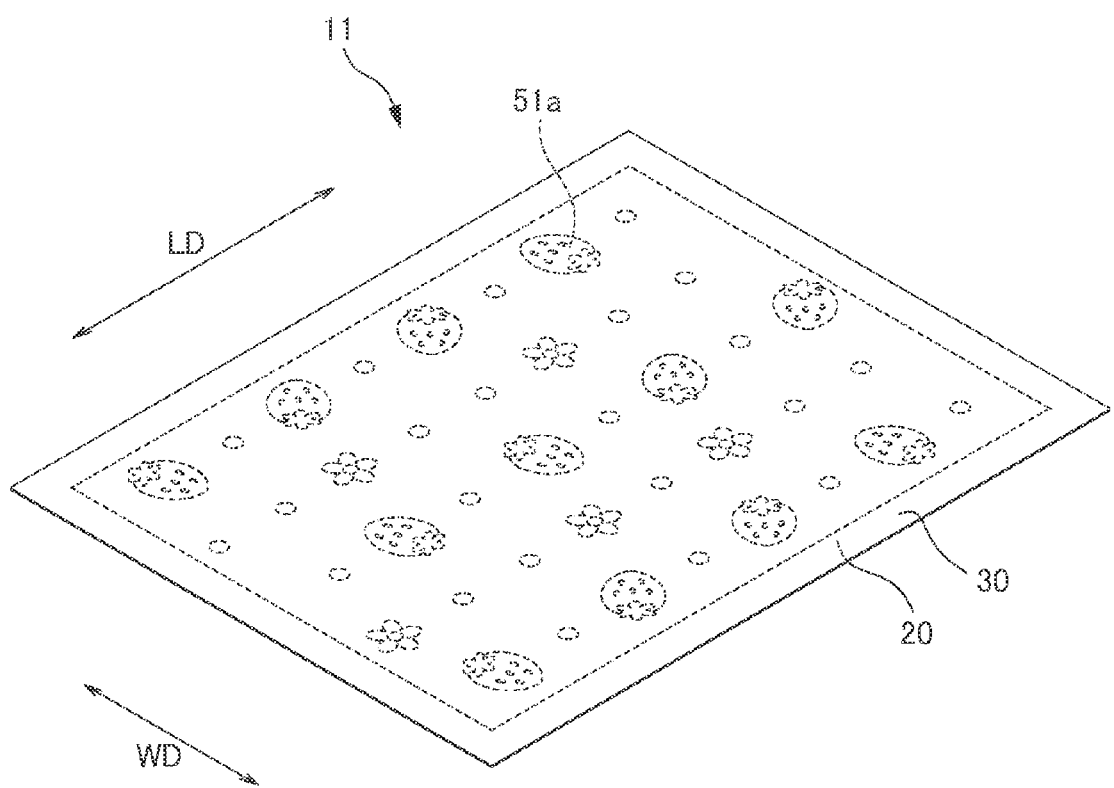
FIG. 6 is a perspective view of the animal excretion disposal sheet of the present invention provided with the evocative pattern as the evocative information, viewed from the back sheet side.

Animal excretion disposal sheets 11 illustrated in FIGS. 5 and 6 have the same basic configuration as the animal excretion disposal sheet 10, and a fragrance ingredient of a strawberry scent is applied thereto as the fragrance ingredient. On the top sheet 20 of the animal excretion disposal sheet 11, an evocative graphic of strawberry fruit and flowers is displayed as the evocative information 51 (51a, 51b). As shown in FIG. 6, the evocative information 51 can be visually recognized as the evocative information 51b from the back sheet 30 side. Similarly to the animal excretion disposal sheet 10 having the evocative color as the evocative information, the animal excretion disposal sheet 11 can allow a consumer or the like, who has visually recognized the evocative graphic 51b from a side of the back sheet 30, to easily recall an image derived from the scent (strawberry scent) from an appearance of the evocative graphic 51b (strawberry figures).

Next, an example of a method for manufacturing the animal excretion disposal sheet 10 is described. In the manufacture of the animal excretion disposal sheet 10, the absorbent body 40 is disposed on a continuous belt-like back sheet material, forming the back sheet 30. When arranging, first a hotmelt adhesive is applied to the back sheet material. A preferable method for applying the hotmelt adhesive is a method of applying it linearly along a flow direction of a manufacturing line, by a contactless coating process such as bead coating. Thereafter, the absorbent body 40 is quickly placed on the back sheet material at predetermined intervals, and the back sheet material and the absorbent body 40 are fixed to each other by adhesion. It should be noted that, as a material for the top face side core wrapping sheet 421 of the absorbent body, a colored tissue dyed in a color which can evoke the scent of the fragrance described below is used. Thereafter, a continuous belt-like top sheet material, which is made to be the top sheet 20, is placed to cover the absorbent body 40, and the back sheet material and the top sheet material are directly bonded to each other by a hotmelt adhesive in a portion where the absorbent body 40 is not present on the back sheet material, to thereby obtain an animal excretion disposal sheet laminated material.

Next, the fragrance is applied to a surface of the top sheet material of the animal excretion disposal sheet laminated material formed through the abovementioned steps. Application of the fragrance can be performed by a well-known coater or the like. The range of application is not particularly limited; however, it is preferable to apply the fragrance only in a region where the top sheet 20 overlaps itself when folded in a later step. This can provide sufficient scent with a small amount of fragrance. This also can avoid negative effects due to the fragrance ingredient attaching to other parts.

After application of the fragrance, the animal excretion disposal sheet laminated material is folded back in a desired folding mode. For example, a triple-fold with the back sheet 30 directed outward as shown in FIG. 4 is preferable. In this case, by setting thicknesses, basis weights and the like of the absorbent body 40 and the back sheet 30 within the above specified ranges, the evocative information 50b can be made visually recognizable even in a state in which the animal excretion disposal sheet 10 is folded.

After folding, the animal excretion disposal sheet laminated material is cut to a predetermined size by a cutter or the like. The animal excretion disposal sheet 10 can thus be manufactured.

The above described animal excretion disposal sheet 10 provides the following effects.

(1) The animal excretion disposal sheet is generally in a state of being folded in a mode in which a back sheet is always directed outward, through distribution stages and between purchase and actual use by a consumer. As a result, the consumer perceives a visual image of the back sheet side as a first impression of the product image at any of the above described stages.

The animal excretion disposal sheet 10 is configured to be the animal excretion disposal sheet 10 including the liquid permeable top sheet 20, the liquid impermeable back sheet 30, and the absorbent body 40 disposed between the top sheet 20 and the back surface sheet 30 that absorbs and retains liquid such as excreted liquid, in which the fragrance ingredient is applied to the top sheet 20 or the absorbent body 40; the evocative information 50 composed of at least one of color, graphic or character that can evoke the scent of the fragrance ingredient is displayed on the top sheet 20 or the absorbent body 40; and the evocative information 50 can be visually recognized from the back sheet 30 side. As a result, by allowing a consumer or the like of the animal excretion disposal sheet 10 to visually recognize the evocative information 50 before use, an image derived from scent can be evoked from the appearance. The image of the animal excretion disposal sheet 10 can thus be improved.

(2) The evocative information 50 is configured to be visually recognizable also from the front sheet 20 side. As a result, the consumer or the like of the animal excretion disposal sheet 10 can visually recognize the evocative information 50 from any of the faces. The effect of improving the product image of the animal excretion disposal sheet 10 can thus be further enhanced.

(3) The evocative information is configured as the evocative color 50 that can evoke the scent of the fragrance ingredient. As a result, the product image derived from the scent of the animal excretion disposal sheet 10 can be intuitively evoked by a simple configuration. The effect of improving the product image of the animal excretion disposal sheet 10 can thus be further enhanced.

(4) A combination of the scent of the fragrance ingredient and the evocative color 50 is configured to be any one of (a) to (d) below. As a result, the product image derived from the appearance of the animal excretion disposal sheet 10 can be evoked more reliably and correctly. In addition, these scents assuredly act as agreeable scents for a user when used indoors. The effect of improving the product image of the scented animal excretion disposal sheet 10 can thus be further ensured.

(a) The scent of the fragrance ingredient is a soapy scent and the evocative color is a whitish or bluish color;

(b) The scent of the fragrance ingredient is a green tea-like scent and the evocative color is a greenish color;

(c) The scent of the fragrance ingredient is a floral scent and the evocative color is a pinkish or yellowish color;

(d) The scent of the fragrance ingredient is a citrus scent and the evocative color is a yellowish or greenish color;

(e) The scent of the fragrance ingredient is a fruity scent and the evocative color is a pinkish yellowish color; and (f) The scent of the fragrance ingredient is a marine scent and the evocative color is a bluish color.

(5) The absorbent body 40 is configured to be provided with the absorbent core 41 and the top face side core wrapping sheet 421 which is disposed on the top sheet 20 side of the absorbent core 41, and the evocative information 50 is configured to be displayed on the top face side core wrapping sheet 421. As a result, the evocative information 50 can thus easily be made visually recognizable from both of the top sheet 20 side and the back sheet 30 side. In addition, by configuring the top face side core wrapping sheet 421 to be colored with the evocative color, the animal excretion disposal sheet 10 can be manufactured with a minimum additional cost.

(6) A basis weight of the top sheet 20 is configured to be at least 23 g/m$^2$ and the sum of the basis weight of the top sheet 20 and the basis weight of the absorbent body 40 is configured to be in a range of 59 g/m$^2$ to 232 g/m$^2$. As a result, the evocative information 50a in the animal excretion disposal sheet 10 can be made easily visually recognizable from the top sheet 20 side and the back sheet 30 side, while maintaining the preferable absorption performance of the animal excretion disposal sheet 10.

(7) In addition, the basis weight of the absorbent body is configured to be in a range of 36 g/m$^2$ to 202 g/m$^2$. As a result, the evocative information 50a in the animal excretion disposal sheet 10 can be made easily visually recognizable particularly from the back sheet 30 side, while maintaining the preferable absorption performance of the animal excretion disposal sheet 10.

(8) Furthermore, the total light transmittance of the back sheet 30 is configured to be in a range of 20% to 90%. As a result, the animal excretion disposal sheet 10 can be configured such that the evocative information 50b can be sufficiently visually recognized particularly from the back sheet 30 side.

(8) Moreover, the total light transmittance is configured to be in a range of 40% to 70%. As a result, the animal excretion disposal sheet 10 can be configured such that the evocative information 50b can be visually recognized more clearly, particularly from the back sheet 30 side.

Next, a package body of the animal excretion disposal sheet is described. As described above, the package body 70 of the animal excretion disposal sheet is the animal excretion disposal sheet 10 folded with the back sheet 30 directed to an outer face side and packaged in a bag 60 made of a resin film.

Figure 7:
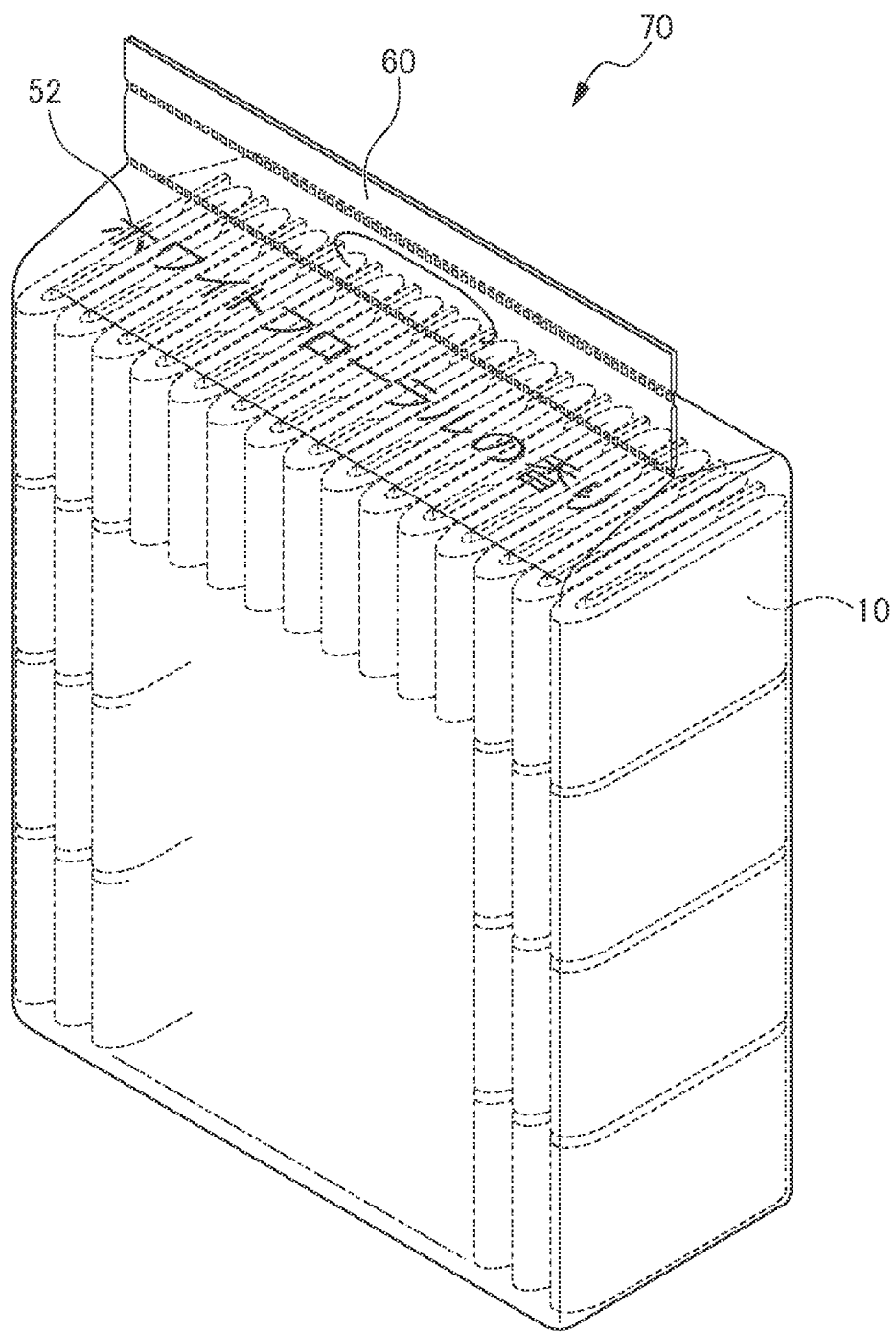
FIG. 7 is a perspective view of a package body of the animal excretion disposal sheet of the present invention.

In the package body 70 of the animal excretion disposal sheet, the animal excretion disposal sheet 10 is disposed in the bag 60 in a state of being folded in a desired mode, as shown in FIG. 7. A method of folding the animal excretion disposal sheet 10 can be adjusted as appropriate according to the size of the animal excretion disposal sheet 10 and the size of the bag 60. As an example, in a case of a sheet of a general size of 440 mm×330 mm, it is preferable to package the sheet, from a triple-folded state with the back sheet 30 constituting the outer face as described above, to a state of being further triple-folded to be reduced in size to half- to quarter-size, from a triple-folded state with the back sheet 30 constituting the outer face as described above. It is preferable to package the animal excretion disposal sheet 10 thus folded tightly in the bag 60 with no space therebetween, in an arrangement shown in FIG. 5, for example.

As the bag 60, a resin film such as polyethylene, polypropylene, polyethylene terephthalate shaped into a bag form can be used. It is preferable that the evocative information 52 is displayed on the bag 60, as illustrated in FIG. 6. It is more preferable that the evocative information 52 is the evocative character 52 composed of a character. By clearly displaying the evocative character 52 on the bag 60, a consumer can correctly understand the type of scent based on the evocative character 52 and then perceive the scent of the fragrance and the evocative color 50b upon opening of the bag 60.

The above described package body 70 of animal excretion disposal sheet provides the following effects.

(10) The package body 70 of animal excretion disposal sheet is configured to include the animal excretion disposal sheet 10 and the bag 60 that houses the animal excretion disposal sheet 10, in which the animal excretion disposal sheet 10 is housed in the bag 60 in a state of being folded with the back sheet 30 constituting the outer face. As a result, a consumer can perceive the evocative color upon opening of the package at the latest.

(11) The animal excretion disposal sheet 10 is configured to be folded so as to have an area in which top sheet 20 portions oppose each other and an area in which the top sheet 20 opposes the back sheet 30, and the fragrance ingredient is configured to be applied to the area in which the top sheet 20 portions oppose each other. This allows the animal excretion disposal sheet 10 to release sufficient scent with a smaller application amount of fragrance, and can suppress dissipation of the fragrance ingredient before opening of the package.

(12) The evocative information 52 is configured to be displayed also on the surface of the bag 60. This allows a consumer of the animal excretion disposal sheet 10 to first perceive the type of scent based on the evocative information 52 before opening the bag 60. Thereafter, the consumer perceives the scent of the fragrance sensorially upon opening the bag 60 while visually recognizing the evocative color 50b. Through such processes, the effect of improving the product image of the animal excretion disposal sheet 10 can thus be further amplified.

An embodiment of the present invention has been explained above; however, the present invention is not limited thereto. It should also be noted that the effects described in the embodiment of the present invention are merely preferred effects of the present invention and the effects of the present invention are not limited thereto.

The animal excretion disposal sheet 10 of the present invention can be used as a toilet for an animal kept as a pet such as a dog, cat, rabbit or the like, and can be particularly preferably used as a toilet for a dog kept indoors.

The invention claimed is:

1. An animal excretion disposal sheet comprising: a liquid permeable top sheet; a liquid impermeable back sheet; and an absorbent body that is disposed between the liquid permeable top sheet and the liquid impermeable back sheet;
    wherein a fragrance ingredient is applied to the top sheet or the absorbent body;
    evocative information composed of at least one of color, graphic and character that can evoke scent of the fragrance ingredient is displayed on the top sheet or the absorbent body; and
    the evocative information can be visually recognized from the back sheet side.

2. The animal excretion disposal sheet according to claim 1, wherein
    the evocative information can also be visually recognized from the top sheet side.

3. The animal excretion disposal sheet according to claim 1, wherein
    the evocative information is an evocative color that can evoke the scent of the fragrance ingredient.

4. The animal excretion disposal sheet according to claim 3, wherein
a combination of the scent of the fragrance ingredient and the evocative color is any one of the following (a) to (f):
(a) the scent of the fragrance ingredient is a soapy scent and the evocative color is a whitish or bluish color;
(b) the scent of the fragrance ingredient is a green tea-like scent and the evocative color is a greenish color;
(c) the scent of the fragrance ingredient is a floral scent and the evocative color is a pinkish or yellowish color;
(d) the scent of the fragrance ingredient is a citrus scent and the evocative color is a yellowish or greenish color;
(e) the scent of the fragrance ingredient is a fruity scent and the evocative color is a pinkish yellowish color; and
(f) the scent of the fragrance ingredient is a marine scent and the evocative color is a bluish color.

5. The animal excretion disposal sheet according to claim 1, wherein
the absorbent body is provided with an absorbent core and a top face side core wrapping sheet which is disposed on the top sheet side of the absorbent core; and
the evocative information is displayed on the top face side core wrapping sheet.

6. The animal excretion disposal sheet according to claim 1, wherein
a basis weight of the top sheet is at least 23 $g/m^2$ and the sum of the basis weight of the top sheet and a basis weight of the absorbent body is in a range of 59 $g/m^2$ to 232 $g/m^2$.

7. The animal excretion disposal sheet according to claim 6, wherein
the basis weight of the absorbent body is in a range of 36 g/m2 to 202 g/m2.

8. The animal excretion disposal sheet according to claim 1, wherein
a total light transmittance of the back sheet is in a range of 20% to 90%.

9. The animal excretion disposal sheet according to claim 8, wherein the total light transmittance is in a range of 40% to 70%.

10. A package body of animal excretion disposal sheet comprising: the animal excretion disposal sheet according to claim 1; and a bag that houses the animal excretion disposal sheet,
wherein the animal excretion disposal sheet is housed in the bag in a state of being folded such that the back sheet composes an outer face.

11. The package body of the animal excretion disposal sheet according to claim 10, wherein
the animal excretion disposal sheet is folded so as to have an area in which portions of the top sheet oppose each other and an area in which the top sheet opposes the back sheet; and
the fragrance ingredient is applied to the area on the top sheet in which portions of the top sheet oppose each other.

12. The package body of the animal excretion disposal sheet according to claim 10, wherein
the evocative information is also displayed on a surface of the bag.

13. The package body of the animal excretion disposal sheet according to claim 11, wherein
the evocative information is also displayed on a surface of the bag.

* * * * *